(12) United States Patent
Lombardo et al.

(10) Patent No.: US 11,612,518 B2
(45) Date of Patent: Mar. 28, 2023

(54) PROCESS FOR DOSING A CHROMOPHORIC AGENT IN A CORNEAL TISSUE AND APPARATUS FOR CONTROLLING THE DOSING

(71) Applicant: Vision Engineering Italy Societa' A Responsabilita' Limitata, Rome (IT)

(72) Inventors: Marco Lombardo, Rome (IT); Giuseppe Lombardo, Rende (IT); Norberto Liborio Micali, Messina (IT); Valentina Villari, Messina (IT)

(73) Assignee: VISION ENGINEERING ITALY SOCIETA' A RESPONSABILITA' LIMITATA, Rome (IT)

( * ) Notice: Subject to any disclaimer, the term of this patent is extended or adjusted under 35 U.S.C. 154(b) by 546 days.

(21) Appl. No.: 16/071,284

(22) PCT Filed: Dec. 21, 2016

(86) PCT No.: PCT/IB2016/057885
§ 371 (c)(1),
(2) Date: Jul. 19, 2018

(87) PCT Pub. No.: WO2017/130043
PCT Pub. Date: Aug. 3, 2017

(65) Prior Publication Data
US 2021/0196511 A1   Jul. 1, 2021

(30) Foreign Application Priority Data
Jan. 26, 2016  (IT) .......................... 102016000007349

(51) Int. Cl.
*A61F 9/008*   (2006.01)
*A61F 9/007*   (2006.01)

(52) U.S. Cl.
CPC ............ *A61F 9/0079* (2013.01); *A61F 9/008* (2013.01); *A61F 2009/0088* (2013.01); *A61F 2009/00872* (2013.01); *A61F 2009/00893* (2013.01)

(58) Field of Classification Search
CPC .. A61F 9/0079; A61F 9/008; A61F 2009/008; A61N 5/062
See application file for complete search history.

(56) References Cited

U.S. PATENT DOCUMENTS

| 8,574,277 B2 | 11/2013 | Muller et al. |
| 2011/0152219 A1 | 6/2011 | Stagni et al. |

(Continued)

FOREIGN PATENT DOCUMENTS

| WO | WO2011130356 | 10/2011 |
| WO | WO2012095876 | 7/2012 |

(Continued)

*Primary Examiner* — Lynsey C Eiseman
(74) *Attorney, Agent, or Firm* — Stetina Brunda Garred & Brucker

(57) ABSTRACT

Control apparatus (1) for controlling the dosing of a chromophoric agent (100) in a corneal tissue (101), comprising: a first source (2) for irradiating the corneal tissue (101) with at least a first electromagnetic radiation (21); first measurement means (3) for measuring a first spectroscopic parameter (31), such as the fluorescence intensity or the diffused intensity; a processing unit (4) configured to calculate a factor (C) representative of the concentration of the chromophoric agent (100) inside the corneal tissue (101) in response to at least two measurements of the first spectroscopic parameter (31), of which one measurement is indicative of the energy perturbation caused by the first electromagnetic radiation (21) in the corneal tissue (101) without the chromophoric agent (100) and the further measurement is indicative of the energy perturbation caused by the first (Continued)

electromagnetic radiation (21) in the corneal tissue (101) containing the chromophoric agent (100).

21 Claims, 9 Drawing Sheets

(56) References Cited

U.S. PATENT DOCUMENTS

| | | | |
|---|---|---|---|
| 2012/0083772 A1 | 4/2012 | Rubinfeld et al. | |
| 2012/0310083 A1* | 12/2012 | Friedman | A61F 9/0079 600/431 |
| 2012/0310141 A1* | 12/2012 | Kornfield | A61F 9/0008 604/20 |
| 2014/0194957 A1* | 7/2014 | Rubinfeld | A61F 9/0079 607/90 |
| 2015/0126921 A1* | 5/2015 | Rubinfeld | A61K 9/0048 604/20 |
| 2020/0107953 A1* | 4/2020 | Adler | A61F 9/0008 |
| 2020/0353279 A1* | 11/2020 | Harhen | A61F 9/007 |

FOREIGN PATENT DOCUMENTS

| | | |
|---|---|---|
| WO | WO2012145853 | 11/2012 |
| WO | WO2013059837 | 4/2013 |

\* cited by examiner

PROCESS FOR DOSING A CHROMOPHORIC AGENT IN A CORNEAL TISSUE AND APPARATUS FOR CONTROLLING THE DOSING

CROSS REFERENCE TO RELATED APPLICATION(S)

The present application claims priority to PCT International Application No. PCT/IB2016/057885 filed on Dec. 21, 2016, which application claims priority to Italian Patent Application No. 102016000007349 filed Jan. 26, 2016, the entirety of the disclosures of which are expressly incorporated herein by reference.

STATEMENT RE: FEDERALLY SPONSORED RESEARCH/DEVELOPMENT

Not Applicable.

TECHNICAL FIELD

The present invention relates to a control apparatus for controlling the dosing of a chromophoric agent in a corneal tissue and a process for dosing a chromophoric agent in a corneal tissue. In particular, the apparatus and the process proposed herewith are used to determine the efficacy of a corneal cross-linking treatment.

BACKGROUND ART

As is well known, keratoconus is a progressive degeneration of the cornea, which tends to thin and curve outwards (it is properly spoken of as "corneal ectasia").

The use of eyeglasses or contact lenses makes it possible to attenuate the symptoms of the pathology, that is, to correct the optical aberrations of the ectatic cornea, but does not halt its progression.

In advanced cases, when the structure of the cornea is by now compromised, it is necessary to have recourse to cornea transplant surgery, or keratoplasty, which consists in the replacement of the ecstatic cornea with a suitable human donor tissue from an eye bank. In order to slow down or halt the progression of keratoconus, in the past decade a parasurgical procedure known in the field as "conical cross-linking" has been introduced.

Corneal cross-linking has the aim of increasing corneal rigidity, which has been reduced as a result of evolutive keratoconus or other iatrogenic corneal ectasias. The list of clinical applications of conical cross-linking is expanding with the development of knowledge on corneal biophysics.

Corneal cross-linking entails the administration of a photopolymerising agent (referred to in the field as "cross-linking" agent) into the conical stroma, followed by photo-activation by irradiation. Photo-activation brings about the creation of new covalent chemical bonds between stromal proteins (one speaks of photopolymerization), with a consequent stiffening of the corneal tissue.

The most common cross-linking agent is riboflavin, which, when subjected to photo-activation, converts the oxygen dissolved in the conical stroma into free radicals. The free radicals, in turn, cause the generation of new covalent bonds between the molecules of the corneal stroma.

For photo-activation use is made, for example, of non-coherent luminous radiation in the ultraviolet (UV-A) or green spectrum. The use of a coherent laser source is also envisaged.

The cross-linking agent is administered in ophthalmic solutions with a known concentration directly onto the conical tissue. In clinical settings, there are various protocols for administering the cross-linking agent, whose variability resides, for example:

in whether or not the conical epithelium is removed prior to administration of the cross-linking agent;
in the duration of administration of the cross-linking agent;
in the method of administration of the cross-linking agent (see documents U.S. Pat. No. 8,574,277, WO 2011/130356, WO 2012/95876);
in the formulation of the ophthalmic solution containing the cross-linking agent, which can vary in terms of viscosity, tone, pH, chemical agents, etc. (see, for example, US 2011/0152219);
in the radiation source selected and the mode of emission of the radiation (e.g. coherent or non-coherent, continuous or pulsed, duration, power density, etc.).

Due to the high differentiation among clinical protocols, corneal cross-linking must be performed by expert medical staff.

Furthermore, the clinical and scientific literature shows highly variable results regarding the efficacy of corneal cross-linking in the treatment of keratoconus, due both to the subjectivity of the operator and the intrinsic heterogeneity of human corneal tissue affected by keratoconus (Chunyu T, Xiujun P, Zhengjun F, Xia Z, Feihu Z. *Corneal collagen cross-linking in keratoconus: a systematic review and meta-analysis*. Sci Report 2014; 4: 5652; Sykasis E, Karim R, Evans J R, Bunce C, Amissah-Arthur K N, Patway S, McDonnell P J, Hamada S. *Corneal collagen cross-linking for treating keratoconus*. The Cochrane collaboration 2015; Issue 3).

One critical aspect of corneal cross-linking treatment is tied to the safety of the treatment, where the power density of the radiation exceeds a certain threshold (e.g. 50 $mW/cm^2$) or the concentration of the cross-linking agent in the stroma is too low (e.g. the riboflavin is less than 0.001%) and the cornea is de-epithelialized. In these cases, the corneal cross-linking treatment, besides not being effective, can damage the corneal endothelial layer, causing irreversible damage to the tissue.

Document WO 2012/145853 discloses a compact apparatus, which is applied on a slit lamp and consists of a proximity sensor that detects the corneal tissue and a sensor for measuring the fluorescence emitted by the cornea saturated with the cross-linking agent (e.g. riboflavin).

However, the document does not propose any method for evaluating the efficacy of the cross-linking treatment.

Document US 2012/083772 discloses a system for corneal cross-linking treatments and methods for dosing the content of oxygen and/or riboflavin in the corneal tissue. This document as well, however, does not aim to evaluate the efficacy of the cross-linking treatment.

Document WO 2013/059837 relates to a method for activating the cross-linking agent by pulsed light and controlling the photopolymerization reaction in the corneal tissue. In this document too, however, there is no aim of evaluating the efficacy of the cross-linking treatment.

To date, the clinical efficacy of corneal cross-linking treatment has been determined by an ophthalmologist who is an expert in the field of application by evaluating and comparing the corneal topography maps of the keratoconus acquired prior to treatment and in the twelve months following the treatment itself.

This is therefore an a posteriori evaluation.

DISCLOSURE OF THE INVENTION

In this context, the technical task at the basis of the present invention is to provide a control apparatus for controlling the dosing of a chromophoric agent in a corneal tissue and a process for dosing a chromophoric agent in a conical tissue which overcome the drawbacks of the aforementioned prior art.

In particular, it is an object of the present invention to provide a process for dosing a chromophoric agent in a corneal tissue which enables the efficacy and safety of the corneal cross-linking treatment to be evaluated in real time, i.e. while it is being performed.

Another object of the present invention is to provide a process for dosing a chromophoric agent in a corneal tissue that is more reliable and efficient than the known methods.

A further object of the present invention is to provide a process for dosing a chromophoric agent in a corneal tissue that can also be implemented by less expert medical personnel.

Another object of the present invention is to provide a control apparatus for controlling the dosing of a chromophoric agent in a corneal tissue which enables the efficacy and safety of the corneal cross-linking treatment to be evaluated in real time, i.e. while it is being performed.

A further object of the present invention is to provide a control apparatus for controlling the dosing of a chromophoric agent in a corneal tissue which is reliable and efficient and can also be used by less expert medical personnel.

The stated technical task and specified objects are substantially achieved by a control apparatus for controlling the dosing of a chromophoric agent in a corneal tissue and a process for dosing a chromophoric agent in a corneal tissue, comprising:
first means for irradiating the corneal tissue with at least a first electromagnetic radiation;
first measurement means for measuring a first spectroscopic parameter;
a processing unit configured to calculate a factor representative of the concentration of the chromophoric agent inside the corneal tissue in response to at least two measurements of the first spectroscopic parameter, of which one measurement is indicative of the energy perturbation caused by the first electromagnetic radiation in the corneal tissue without the chromophoric agent and the further measurement is indicative of the energy perturbation caused by the first electromagnetic radiation in the conical tissue containing the chromophoric agent.

In one embodiment, the first irradiating means consist in a source configured to emit the first electromagnetic radiation with a wavelength selected so as to cause the fluorescence effect and the first measurement means are configured to measure the fluorescence intensity.

Alternatively, the first irradiating means consist in a source configured to emit the first electromagnetic radiation with a wavelength selected so as to be absorbed by the chromophoric agent and the first measurement means are configured to measure the diffused intensity.

For example, the first measurement means comprise a video camera or a spectrometer or one or more photodiodes.

The means used to transmit the first electromagnetic radiation to the corneal tissue is air or an optical fibre.

The means used to receive the energy perturbation caused by the first electromagnetic radiation is air or a further optical fibre.

The stated technical task and specified objects are substantially achieved by a process for dosing a chromophoric agent in a corneal tissue, comprising the steps of:
subjecting the conical tissue to at least a first electromagnetic radiation;
performing a measurement of a first spectroscopic parameter, indicative of the energy perturbation caused by the first electromagnetic radiation in the corneal tissue;
as long as a factor representative of the concentration of the chromophoric agent in the corneal tissue remains below a first pre-established threshold, cyclically performing at least the following steps in chronological order:
administering the chromophoric agent to the conical tissue;
subjecting the corneal tissue containing the chromophoric agent to the first electromagnetic radiation;
performing a further measurement of the first spectroscopic parameter, indicative of the energy perturbation caused by the first electromagnetic radiation in the corneal tissue containing the chromophoric agent;
calculating the factor representative of the concentration of the chromophoric agent inside the corneal tissue as a function at least of the measurement and of the further measurement of the first spectroscopic parameter.

In one embodiment, the chromophoric agent is a fluorophore and the first electromagnetic radiation has a wavelength selected so as to cause the fluorescence effect of the fluorophoric agent. The first spectroscopic parameter is thus the fluorescence intensity, so that the measurement of the first spectroscopic parameter corresponds to the value of the fluorescence intensity of the corneal tissue without the fluorophoric agent and the further measurement of the first spectroscopic parameter corresponds to the value of the fluorescence intensity of the corneal tissue containing the fluorophoric agent.

In one embodiment, the first electromagnetic radiation has a wavelength selected so as to be absorbed by the chromophoric agent. The first spectroscopic parameter is thus the diffused intensity, so that the measurement of the first spectroscopic parameter corresponds to the value of the intensity diffused by the corneal tissue without the chromophoric agent and the further measurement of the first spectroscopic parameter corresponds to the value of the intensity diffused by the corneal tissue containing the chromophoric agent.

In the event of use of the fluorophoric agent, according to one embodiment the process can also comprise the following steps:
subjecting the corneal tissue without the fluorophoric agent to a second electromagnetic radiation having a wavelength selected so as to be absorbed by the fluorophoric agent;
performing a measurement of the intensity diffused by the corneal tissue without the fluorophoric agent;
as long as the factor representative of the concentration is below the pre-established threshold ($T_{h1}$), cyclically performing also the following steps:
after performing the further measurement of the first spectroscopic parameter, subjecting the corneal tissue containing the chromophoric agent to the second electromagnetic radiation;
performing a further measurement of the intensity diffused by the corneal tissue containing the fluorophoric agent, also using, when calculating the factor of concentration of the fluorophoric agent inside the corneal tissue, the measurement and the further measurement of the diffused intensity.

In one embodiment, the process comprises a step of photo-activating the chromophoric agent, after the factor representative of the concentration equals or exceeds the first pre-established threshold.

It can also comprise a step of estimating the mechanical stiffening of the corneal tissue as a function of the values taken on by the factor representative of the concentration before and after the photo-activating step.

Preferably, the step of estimating the mechanical stiffening of the corneal tissue comprises a step of iteratively modifying the pattern of photo-activating intensity of the first electromagnetic radiation as long as the predicted value of the mechanical stiffening Y is below an efficacy threshold.

BRIEF DESCRIPTION OF DRAWINGS

Additional features and advantages of the present invention will become more apparent from the approximate, and hence non-limiting, description of a preferred, but non-exclusive, embodiment of a control apparatus for controlling the dosing of a chromophoric agent in a corneal tissue and a process for dosing a chromophoric agent in a corneal tissue, as illustrated in the appended drawings, in which.

DETAILED DESCRIPTION OF PREFERRED EMBODIMENTS OF THE INVENTION

Figure 1:
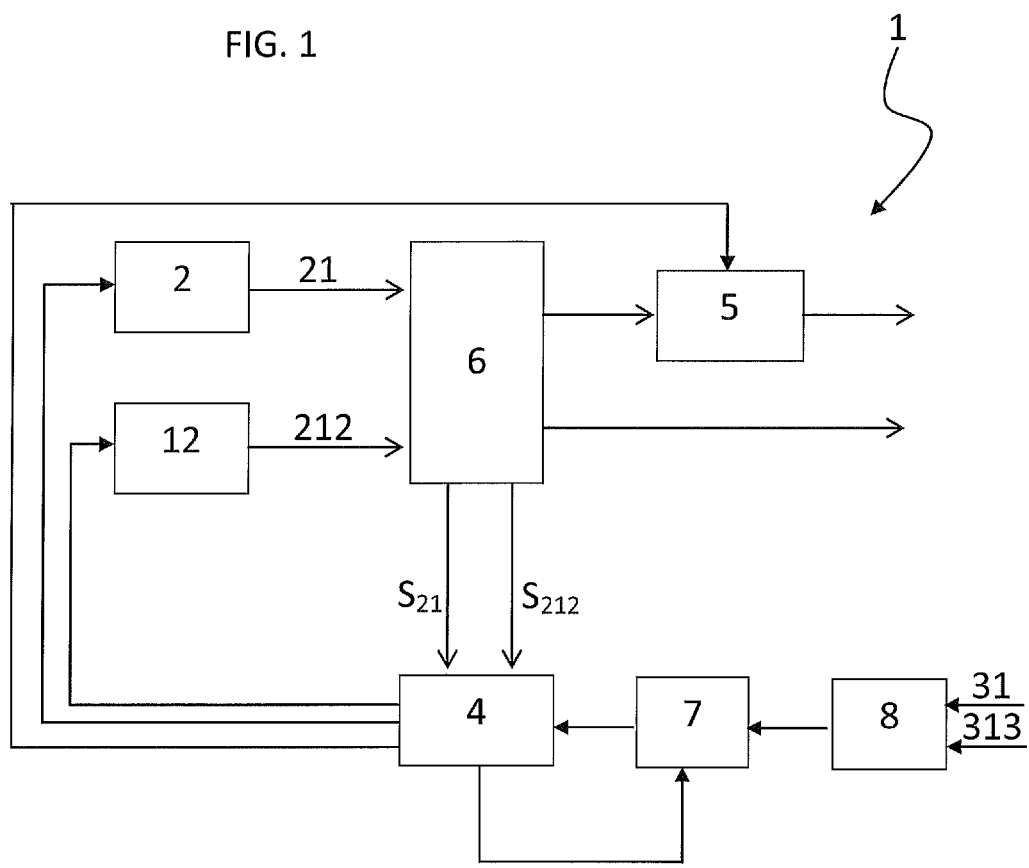
FIG. 1 illustrates a simplified block diagram of a control apparatus for controlling the dosing of a chromophoric agent in a corneal tissue, according to the present invention, in a third embodiment.

In reference to the figures, the number 1 denotes a control apparatus for controlling the dosing of a chromophoric agent 100 in a corneal tissue 101.

In this context, the corneal tissue 101 is assumed to be like a portion of a sphere having an optical axis r passing through the centre of the sphere O.

The control apparatus 1 comprises:
first means for irradiating 2 the corneal tissue 101 with at least a first electromagnetic radiation 21;
first measurement means 3 for measuring a first spectroscopic parameter 31.

In a first embodiment, which can be used when the chromophoric agent 100 is a fluorophore, the first irradiating means 2 consist in a source configured to emit the first electromagnetic radiation 21 with a wavelength $\lambda_{21}$ selected so as to cause the fluorescence effect in the fluorophoric agent 100.

In this embodiment, the first measurement means 3 are configured to measure the fluorescence intensity (which represents the first spectroscopic parameter 31). For example, the first measurement means 3 consist in an RGB video camera configured to measure the average intensity value of the green pixels of the acquired image.

In a second embodiment, the first irradiating means 2 consist in a source configured to emit the first electromagnetic radiation 21 with a wavelength $\lambda_{21}$ selected so as to be absorbed by the chromophoric agent 100 (be it a fluorophore or not a fluorophore).

In this embodiment, the first measurement means 3 are configured to measure the diffused intensity (which represents the first spectroscopic parameter 31). For example, the first measurement means 3 consist in an RGB video camera configured to measure the average intensity value of the blue pixels of the acquired image.

In all the embodiments, the control apparatus 1 comprises a processing unit 4 configured to calculate a factor C representative of the concentration of the chromophoric agent 100 inside the corneal tissue 101 in response to measurements of the first spectroscopic parameter 31 performed by the first measurement means 3.

In particular, the processing unit 4 receives as input at least two measurements of the first spectroscopic parameter 31:
one measurement is indicative of the energy perturbation caused by the first electromagnetic radiation 21 in the corneal tissue 101 without the chromophoric agent 100;
a further measurement is indicative of the energy perturbation caused by the first electromagnetic radiation 21 in the corneal tissue 101 containing the chromophoric agent 100.

In a third embodiment, illustrated in FIG. 1, the control apparatus 1 further comprises:
second means for irradiating 12 the corneal tissue 101 with a second electromagnetic radiation 212;
second measurement means 13 for measuring a second spectroscopic parameter 313.

In this embodiment, the first irradiating means 2 consist in a source (hereinafter called "first source") configured to emit the first electromagnetic radiation 21 with a wavelength $\lambda_{21}$ selected so as to cause the fluorescence effect in the chromophoric agent 100, whilst the second irradiating means 12 consist in a source (hereinafter indicated as "second source") configured to emit the second electromagnetic radiation 212 with a wavelength $\lambda_{212}$ selected so as to be absorbed by the chromophoric agent 100 (fluorophore or non-fluorophore).

In this embodiment, the first measurement means 3 are configured to measure the fluorescence intensity (which represents the first spectroscopic parameter 31), whilst the second measurement means 13 are configured to measure the diffused intensity (which represents the second spectroscopic parameter 313).

For example, the first measurement means 3 consist in an RGB video camera configured to measure the average intensity value of the green pixels of the acquired image.

For example, the second measurement means 13 consist in an RGB video camera configured to measure the average intensity value of the blue pixels of the acquired image.

In particular, the second source 12 is disposed in such way that the second electromagnetic radiation 212 strikes the conical tissue 101 forming an angle □ comprised between 0° and 90° relative to the optical axis r.

Preferably, the control apparatus 1 comprises collimating means 5 for collimating the first electromagnetic radiation 21 on the conical tissue 101. In particular, the collimating means 5 consist in an optical system capable of focusing and modifying the wave front of the first electromagnetic radiation 21.

Preferably, the control apparatus 1 comprises a measurement unit for measuring the power density 6 of the first electromagnetic radiation 21 and of the second electromagnetic radiation 212.

Preferably, the first measurement means 3 and the second measurement means 13 consist in a single video camera 7 for acquiring images of the corneal tissue 101.

In particular, in the video camera 7 there is an optical sensor capable of extracting the RGB channels. The optical sensor is of the CMOS (acronym of the expression "Complementary Metal Oxide Semiconductor") or CCD (acronym of the expression "Charge Coupled Device") type.

Preferably, the control apparatus 1 further comprises a lens or a system of lenses 8 for focusing the acquired images on the video camera 7.

In this embodiment, the processing unit 4 is thus configured to calculate the factor C representative of the concentration of the chromophoric agent 100 inside the corneal tissue 101 in response to the images acquired by the video camera 7.

The processing unit 4 is further configured to receive signals from the power density measurement unit 6 which are representative of the power density $S_{21}$, $S_{212}$ of the electromagnetic radiation 21, 212 issued and, in response to this:
- adjust the intensity of the first source 2 and/or of the second source 12 (or switch on/off one of sources 2, 12) so that the power density of the electromagnetic radiation 21, 212 remains within the safety intervals for the corneal tissue 101;
- adjust one or more parameters of the video camera 7, such as, for example, exposure, acquisition frequency, gamma correction factor and the infrared filter pre-processing parameter, in such a way that the intensity of the image acquired by the video camera 7 has a wider dynamic interval and is proportional to the number of photons acquired in the spectral band selected by the RGB channels.

In particular, the processing unit 4 employs hyperspectral techniques of a known type, such as Wiener estimation, starting from the images acquired by the RGB video camera 7. The processing unit 4 can consist of an electronic device, suitably programmed to perform the described functions, which can have corresponding to it various hardware and/or routine software entities making up the programmed device.

Alternatively, or in addition, such functions can be performed by a plurality of electronic devices over which an equal number of functional modules can be distributed.

The processing unit 4 can further avail itself of one or more processors for executing instructions contained in memory modules.

Furthermore, the various functional modules can be distributed over local or remote computers based on the architecture of the network they reside in.

Figure 2:
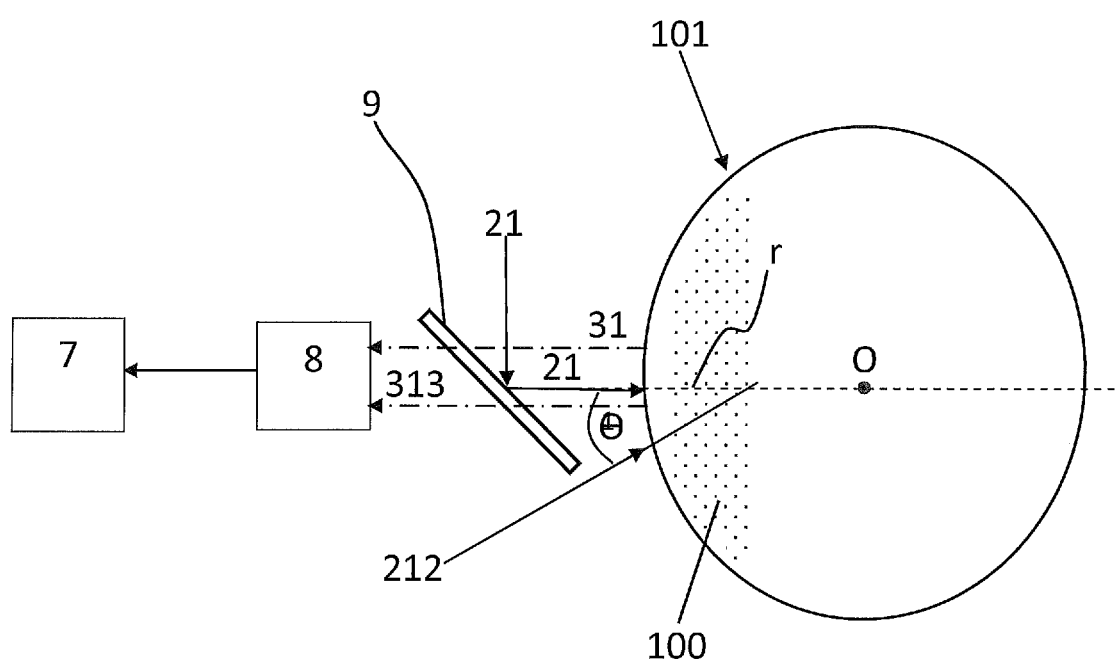
FIGS. 2 and 3 illustrate part of the block diagram in FIG. 1, in the same number of variant embodiments.

In one variant, illustrated in FIG. 2, the control apparatus 1 comprises a dichroic filter 9 placed downstream of the first source 2 so as to receive the first electromagnetic radiation 21 and deliver it to the corneal tissue 101. The dichroic filter 9 has a spectral response such as to transmit the fluorescence radiation and the intensity diffused by the corneal tissue 101 when saturated by the chromophoric agent 100.

In one variant, in the place of the video camera 7, a spectrometer (of a known type) is used to measure the fluorescence intensity and the diffused intensity.

Figure 3:
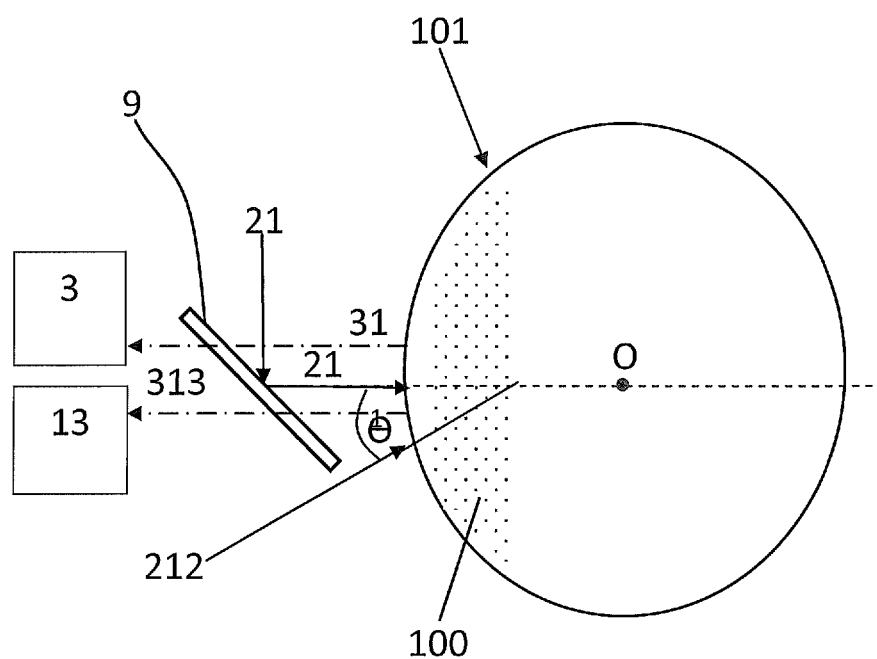

In one variant, illustrated in FIG. 3, the first measurement means 3 and the second measurement means 13 are distinct and consist respectively in a first photodiode 3 configured to measure the fluorescence intensity 31 and a second photodiode 13 configured to measure the intensity 313 diffused by the corneal tissue 101.

The structure of the different components of the control apparatus 1 described for the third embodiment can also be used for the first and second embodiments, except for the duplication of the signals, due to the fact that in the third embodiment two sources are used and thus two distinct spectroscopic parameters are measured.

As regards the first embodiment (based on measurement of the fluorescence intensity), the first irradiating means 2 can consist in a non-coherent light source or in a laser source configured to transmit photons in a continuous or pulsed mode with wavelengths comprised in an interval from ultraviolet (UV-A) to near or mid infrared (NIR or MIR).

In such a manner, photo-activation of the fluorophoric agent 100 in the corneal tissue 101 can take place by absorption of non-coherent light or absorption of a single photon at a given wavelength (for example UV) or by absorption of two or more photons having longer wavelengths, for example NIR or MIR, in such a way that the striking photons penetrate more deeply into the corneal tissue 101 than photons with a shorter wavelength.

In the various embodiments described here, air is used as the transmitting means in order to deliver electromagnetic radiation to the corneal tissue 101. Alternatively, the use of an optical fibre (not illustrated) is envisaged as a transmitting means.

Analogously, in addition to air, another optical fibre (not illustrated) can be used as a means for measuring the energy perturbation caused by the electromagnetic radiation in the corneal tissue 101.

In other words, all the following combinations are possible:
air for delivery, air for recovery;
air for delivery, fibre for recovery;
fibre for delivery, fibre for recovery;
fibre for delivery, air for recovery.

The process for dosing a chromophoric agent in a corneal tissue, according to the present invention, is described below.

First of all, it comprises two steps performed only once:
subjecting the conical tissue 101 at least a first electromagnetic radiation 21;
performing a measurement of the first spectroscopic parameter 31, indicative of the energy perturbation caused by the first electromagnetic radiation 21 in the conical tissue 101.

In the first embodiment, the process envisages that the first electromagnetic radiation 21 has a wavelength $\lambda_{21}$ selected so as to cause the fluorescence effect in the fluorophoric agent 100.

In this first embodiment, the first spectroscopic parameter 31 is the fluorescence intensity.

In the second embodiment, the process envisages that the first electromagnetic radiation 21 has a wavelength $\lambda_{21}$ selected so as to be absorbed by the chromophoric agent 100.

In the second embodiment, the first spectroscopic parameter 31 is the diffused intensity.

The process then comprises cyclically performing at least the following steps:
administering the chromophoric agent 100 to the corneal tissue 101;
subjecting the corneal tissue 101 containing the chromophoric agent 100 to the first electromagnetic radiation 21, whose power density $S_{21}$ is within a first safety interval for the conical tissue 101;
performing a further measurement of the first spectroscopic parameter 31, indicative of the energy perturbation caused by the first electromagnetic radiation 21 in the corneal tissue 101 containing the chromophoric agent 100;
calculating the factor C representative of the concentration of the chromophoric agent 100 inside the corneal tissue 101 as a function at least of the measurement and of the further measurement of the first spectroscopic parameter 31.

These steps are performed cyclically as long as the factor C representative of the concentration of the chromophoric agent 100 in the corneal tissue 101 remains below a first pre-established threshold $T_{h1}$.

In a third embodiment, the first electromagnetic radiation 21 has a wavelength $\lambda_{21}$ selected so as to cause the fluorescence effect in the fluorophoric agent 100 and the first spectroscopic parameter 31 is the fluorescence intensity.

The second electromagnetic radiation 212 instead has a wavelength $\lambda_{212}$ selected so as to be absorbed by the chromophoric agent 100 (fluorophore or non-fluorophore) and the second spectroscopic parameter 313 is the diffused intensity.

Furthermore, the process comprises the following steps (performed only once):
subjecting the corneal tissue 101 without the chromophoric agent 100 to a second electromagnetic radiation 212 having a wavelength selected so as to be absorbed by said chromophoric agent 100;
performing a measurement of the intensity diffused 313 by the corneal tissue 101 without the chromophoric agent 100.

In sequential terms, in the third embodiment one proceeds in this manner
the first source 2 is switched on;
the intensity of the first source 2 is adjusted so that the power density $S_{21}$ remains within a first safety interval;
a measurement of fluorescence intensity 31 is performed on the corneal tissue 101 without the chromophoric agent 100;
the first source 2 is switched off;
the second source 12 is switched on;
the intensity of the second source 12 is adjusted so that the power density $S_{212}$ remains within a second safety interval;
a measurement of the intensity diffused 313 by the corneal tissue 101 is performed without the chromophoric agent 100.

The first and second safety intervals are selected in such a way that the radiation of the sources 2, 12 does not photo-activate the chromophoric agent 100 and is safe for the corneal tissue 101.

For example, the first safety interval is comprised between 0.01 mW/cm$^2$ and 3 mW/cm$^2$, and the second safety interval is comprised between 0.01 mW/cm$^2$ and 10 mW/cm$^2$.

One then proceeds to perform the cycle, composed at least of the sequence of steps below:
administering the chromophoric agent 100 in a known concentration within an ophthalmic solution on the corneal tissue 101;
switching on the first source 2;
adjusting the intensity of the first source 2 so that the power density $S_{21}$ remains within the first safety interval;
subjecting the corneal tissue 101 containing the chromophoric agent 100 to the first electromagnetic radiation 21;
performing a further measurement of the intensity of the fluorescence 31 emitted by the corneal tissue 101 containing the chromophoric agent 100;
switching off the first source 2;
switching on the second source 12;
adjusting the intensity of the second source 12 so that the power density $S_{212}$ remains within the second safety interval;
subjecting the corneal tissue 101 containing the chromophoric agent 100 to the second electromagnetic radiation 212;
performing a further measurement of the intensity diffused 313 by the corneal tissue 101 containing the chromophoric agent 100;
calculating the factor C of concentration of the chromophoric agent 100 inside the corneal tissue 101 using the measurement and the further measurement of the fluorescence intensity 31 and of the diffused intensity 313.

These steps are cyclically performed as long as the factor C representative of the concentration of the chromophoric agent 100 in the corneal tissue 101 remains below the first pre-established threshold $T_{h1}$.

For example, the factor C representative of the concentration is obtained as a linear combination of:
a first concentration $c_1$ of the chromophoric agent 100 in the corneal tissue 101 after the irradiation of the first source 2;
a second concentration $c_2$ of the chromophoric agent 100 in the corneal tissue 101 after the irradiation of the second source 12.

In order to calculate the factor C representative of the concentration based on the spectrometry measurements (in general: fluorescence intensity and/or diffused intensity; in particular: average intensity value of the green and/or blue pixels) known functions and algorithms are used.

For example, as the chromophoric agent 100 (and fluorophore) use is made here of riboflavin, for which the excitation wavelength $\lambda_E$ (i.e. the wavelength $\lambda_{21}$ of the first electromagnetic radiation 21) is selected between 360 nm and 375 nm (to obtain the fluorescence effect), whilst the wavelength $\lambda_{212}$ of the second electromagnetic radiation 212 is selected between 400 nm and 500 nm (absorbance interval of riboflavin).

For example, in the case of riboflavin administered in an ophthalmic solution at a known concentration of 0.1% directly on the corneal tissue, the first pre-established threshold $T_{h1}$ of the factor C is equal to 0.010%.

The fluorescence measurement is based on the exchange of energy that takes place between the first electromagnetic radiation 21 and the fluorophoric agent 100. In particular, the absorption of the energy carried by the first electromagnetic radiation 21 is capable of triggering in the fluorophoric agent 100 energy transitions of the outer electrons, whether or not they are engaged in a chemical bond. The fluorophoric agent 100, excited at a higher vibrational sublevel, can thus relax quickly by non-radiative decay to the lower vibrational level and from this it can decay radiatively to the fundamental state, emitting a photon with a lower energy than the absorbed one.

This physical phenomenon is known precisely as the "fluorescence effect".

For riboflavin, the fluorescence measurement takes place at an emission wavelength $\lambda_F$ comprised between 520 nm and 540 nm.

If $I_F$ is the stationary fluorescence intensity measured at a specific wavelength $\lambda_F$ emitted by the fluorophoric agent 100, it will be proportional both to the emission spectrum F of the fluorophoric agent 100 and the intensity of absorbed light $I_A$ at the excitation wavelength $\lambda_E$, by virtue of the quenching function h(c, T), where c is the concentration and T is the temperature in Kelvin.

The fluorescence intensity formula is:

$$I_F(\lambda_F) = h(c,T)F(\lambda_F)I_A(\lambda_E)$$

For low concentrations of the fluorophoric agent 100 (Lambert-Beer law) and at a given temperature, T, the intensity of absorbed light $I_A$ ($\lambda_E$) is proportional to the optical absorption $a(\lambda_E)$ of the fluorophoric agent 100 and the intensity of incident light $I_0(\lambda_E)$.

In the formula:

$$I_A(\lambda_E) = I_0(\lambda_E)a(\lambda_E)$$

From this it follows that:

$$I_F(\lambda_F) = h(c,T)F(\lambda_F)I_0(\lambda_E)a(\lambda_E)$$

From the latter formula it may be deduced that the fluorescence intensity $I_F(\lambda_F)$ is proportional to the concentration c of the fluorophoric agent 100, by virtue of its optical absorption $a(\lambda_E)$.

As regards the diffused intensity measurement, the phenomena at the basis of the interaction between radiation and matter are diffusion and absorption.

Diffusion (more commonly known by the term scattering) is a physical process whereby tissue diffuses radiation in all directions, maintaining the same wavelength of the incident radiation $\lambda_E$.

In the absence of a chromophoric agent 100 in the corneal tissue 101, the diffused electromagnetic field is not attenuated and a strong diffused signal will be detected. In the presence of a chromophoric agent 100 in the conical tissue 101, by contrast, part of the intensity of the incident radiation will be absorbed by the chromophoric agent 100 and thus the diffused signal will have a lower intensity than the diffused signal in the absence of the chromophoric agent 100.

The well-known Kubelka-Munk theory correlates the diffuse reflectance, $R(\lambda_E)$, i.e. the ratio between the intensity of the electromagnetic radiation diffused in the presence of the chromophoric agent 100 inside the corneal tissue 101 and the intensity of the radiation diffused by the corneal tissue 101 without the chromophoric agent 100, with an absorption coefficient $K(\lambda_E)$ and a characteristic diffusion (scattering) coefficient of the tissue $S(\lambda_E)$:

$$G(R(\lambda_E)) = \frac{(1-R(\lambda_E))^2}{2R(\lambda_E)} = \frac{K(\lambda_E)}{3(\lambda_E)}$$

Assuming that ocular tissue is transparent at the wavelength $\lambda_E$ of the incident radiation, the coefficient $K(\lambda_E)$ directly depends on the absorption properties of the chromophoric agent 100 and thus its concentration c.

The coefficient $S(\lambda_E)$ depends on the microstructure of the conical tissue 101 and, as such, is specific to each eye.

As already noted above, the processing unit 4 employs hyperspectral techniques of a known type, such as the Wiener estimation, starting from images acquired by an RGB 7 video camera.

The Wiener estimation, by taking account of a priori information obtained with spectral analysis on known standard samples, is able to establish a statistical correlation between the RGB values acquired by the video camera 7 and the reference optical spectrum (P. Stigell, K. Miyata, M. Hauta-Kasari. *Wiener Estimation Method in Estimating of Spectral Reflectance from RGB Images.* Pattern Recognition and Image Analysis 2007 (17) 2: 233-242). In particular, the relationship that links the acquired RGB values and the estimated spectral values is the following:

$$r_{estimate} = Gv$$

where v is a column vector containing the RGB intensity, G is the Wiener matrix, estimated with known prior art techniques, and $r_{estimate}$ is the column vector corresponding to the spectral components corresponding to the RGB intensity values. If the chromophoric agent 100 (fluorophore or non-fluorophore) has a fluorescence emission band and/or absorbance inside the individual bands filtered only by the RGB filters of the camera, the $r_{estimate}$ equation given above becomes a linear relationship of equality between the RGB pixel intensity value and the corresponding value of the reference spectral component. For example, if the chromophoric agent 100 is riboflavin, whose absorbance spectrum falls inside the blue filter of the video camera 7 and whose fluorescence emission spectrum falls inside the green filter of the video camera 7, we can simplify the equation into the two following equations:

$$I_{Fluo} = M_{FluoG}$$

and $$I_{Rifl} = M_{RiflB}$$

where the value $$M_{FluoG} = \frac{\sum_{i=1}^{N} I_{FluoCi}}{N}$$

is the average intensity of N pixels contained inside a region of interest, whose i-th pixels take on an intensity value inside the green filter, $I_{FluoGi}$, when the corneal tissue 101 is illuminated by the photo-activation radiation, and $$M_{RifB} = \frac{\sum_{i=1}^{N} I_{RifBi}}{N}$$

is the average intensity of N pixels contained inside a region of interest, whose i-th pixels take on an intensity value inside the blue filter, when the corneal tissue 101 is illuminated by the radiation 31. Thus the first of the two equations associates the average intensity value of the green pixels, $M_{FluoG}$, with the spectral value $I_{Fluo}$, and the second equation associates the average intensity value of the blue pixels, $M_{RifB}$, with the diffused intensity value $I_{Rif}$.

After a procedure of calibration of the control apparatus 1, which enables a calculation of the average value of the intrinsic fluorescence intensity of the corneal tissue 101 without the fluorophoric agent, $B_{KG}=M_{FluoG}$, when illuminated by the first electromagnetic radiation 21, it will be possible afterward to calculate the actual value of the fluorescence, $I_F=I_{Fluo}-B_{KG}$, emitted by the corneal tissue 101 when saturated with the fluorophoric agent and make that value equal to $I_F(\lambda_F)$ in order to derive the concentration of the agent itself in the corneal tissue 101.

Similarly, after a procedure of calibration of the control apparatus 1 used to measure the average value of the intensity diffused by the corneal tissue 101 without the chromophoric agent, $B_{KB}=M_{RifB}$, when illuminated by the second electromagnetic radiation 212, it will be possible afterwards to associate the value of the diffuse reflectance at $R=I_{Rif}/B_{KB}$ and make that value equal to $R(\square_E)$ in order to calculate the actual concentration of the chromophoric agent in the corneal tissue 101 by means of the equation $G(R(\square_E))$ given above.

In practical terms, the Kubelka-Munk theory is valid when the material illuminated by radiation is sufficiently thick, more than 50% of the light is diffused and less than 20% is transmitted, relative to the incident light. In the specific case of corneal tissue 101, this simplification is still valid, as demonstrated by experimental laboratory tests conducted on human corneal tissues from different donors cultured in an eye bank. Once the first pre-established threshold $T_{h1}$ for the factor C of the chromophoric agent 100 is reached or exceeded in the corneal tissue 101, the process further comprises a step of photo-activating the chromophoric agent 100.

The accuracy in the measurement of the concentration of the chromophoric agent 100 (fluorophore or non-fluorophore) with the two spectral methods specified above depends on the interval of the measured concentration. In the case of low concentrations, the Kubelka-Munk method yields more precise values than the fluorescence measurement method. Conversely, in the case of high concentrations, the fluorescence measurement method yields more precise values than the Kubelka-Munk method.

A further distinction between the two spectral methods is that the Kubelka-Munk method can be used for chromophoric agents (fluorescent and non-fluorescent), whereas the fluorescence measurement method can be used exclusively for fluorescent agents.

From a technical viewpoint, by following the administration of the chromophoric agent 100 with the photo-activation thereof, one obtains an authentic cross-linking treatment of the corneal tissue 101.

It should be noted here that, in the case of fluorescent agents (e.g. riboflavin), the method used to determine the concentration by measuring the fluorescence emitted both during the step of administering the fluorescent agent and during the photo-activating step, enables real-time monitoring of the efficacy of the corneal cross-linking treatment. Monitoring the consumption of riboflavin in the corneal tissue 101 will prove advantageous, as described further below.

It should further be pointed out that in the case of fluorescent agents (e.g. riboflavin) the combination of the two methods (Kubelka-Munk and fluorescence measurement) enables a more robust determination of the corneal content of the agent, both at high concentrations (for example at the start of the cross-linking treatment) and low concentrations (at the end of the treatment).

The first pre-established threshold $T_{h1}$ represents the threshold of concentration of the chromophoric agent 100 administered to the corneal tissue 101 prior to the photo-activating step.

The photo-activating step comprises the following sub-steps, performed cyclically:
  switching on the first source 2;
  adjusting the intensity of the first source 2 so that the power density $S_{21}$ is equal to or greater than the first safety interval and such as to photo-activate the chromophoric agent 100;
  subjecting the corneal tissue 101 containing the chromophoric agent 100 to the first electromagnetic radiation 21;
  performing a further measurement of the intensity of the fluorescence 31 emitted by the corneal tissue 101 containing the chromophoric agent 100;
  switching off the first source 2;
  switching on the second source 12;
  adjusting the intensity of the second source 12 so that the power density $S_{212}$ is equal to the second safety interval;
  subjecting the corneal tissue 101 containing the chromophoric agent 100 to the second electromagnetic radiation 212;
  performing a further measurement of the intensity diffused 313 by the corneal tissue 101 containing the chromophoric agent 100;
  calculating the factor C' of concentration of the chromophoric agent 100 inside the corneal tissue 101 using the measurement and the further measurement of the fluorescence intensity 31 and of the diffused intensity 313.

These steps are cyclically performed as long as the factor C' representative of the concentration of the chromophoric agent 100 in the corneal tissue 101 remains above a second pre-established threshold $T_{h2}$.

For example, the factor C' representative of the concentration is obtained here as a linear combination of:
  a first concentration $c_1'$ of the chromophoric agent 100 in the corneal tissue 101 after the irradiation of the first source 2 (which has activated the chromophoric agent 100);
  a second concentration $c_2'$ of the chromophoric agent 100 in the corneal tissue 101 after the irradiation of the second source 12.

The first and second safety intervals are selected in such a way that the radiation of the first source 2 can photo-activate the chromophoric agent 100 in the corneal tissue 101 and the radiation from both sources 2, 12 is safe for the corneal tissue 101.

Figure 4:
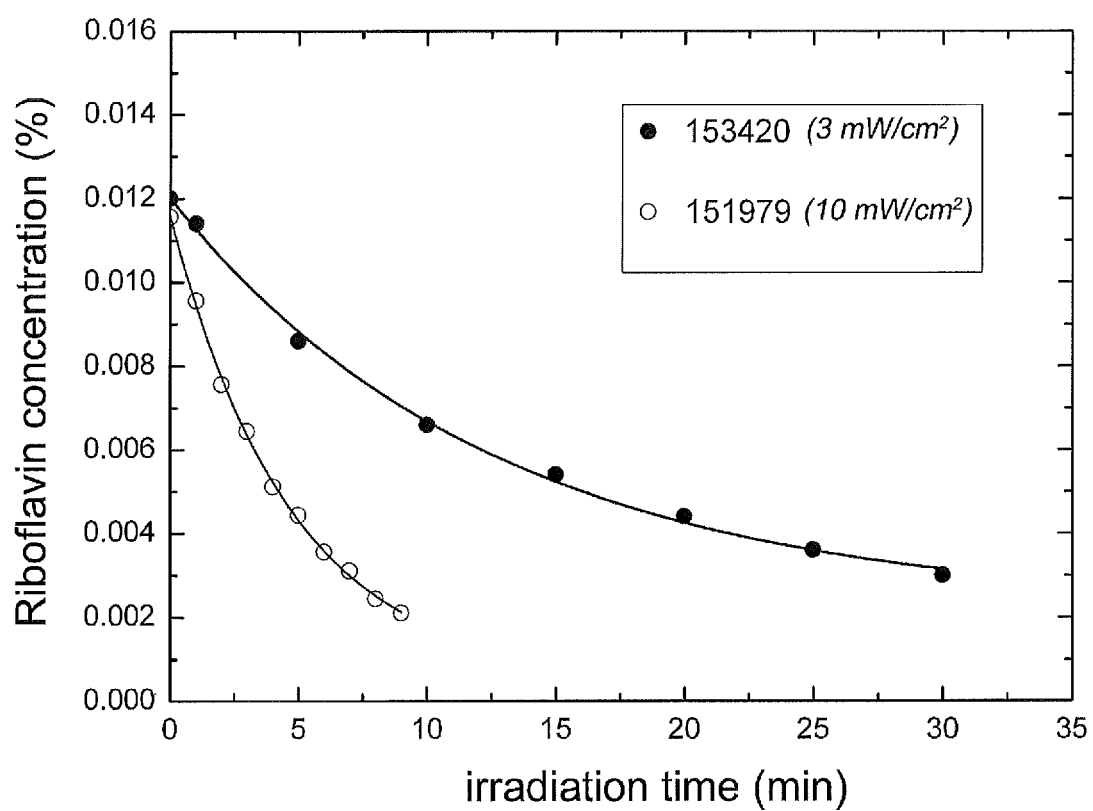
FIG. 4 represents the curves of the percent concentration of riboflavin (y-axis) as a function of the irradiation time in minutes (x-axis) recorded for different power densities of UV-A radiation.

For example, the first safety interval is comprised between 3 mW/cm$^2$ and 45 mW/cm$^2$, and the second safety interval is comprised between 0.01 mW/cm$^2$ and 10 mW/cm². The second pre-established threshold $T_{h2}$ represents the threshold of concentration of the chromophoric agent 100 in the corneal tissue 101 immediately after the photo-activating step. FIG. 4 shows the percent concentration of riboflavin (y-axis) as a function of the irradiation time in minutes (x-axis) recorded for different power densities of the UV-A radiation (in the figure the radiation at 370±5 nm is represented) in two different corneal tissues (indicated with different numbers and symbols) representative of the riboflavin concentrations during the photo-activating step at two different UV-A power densities.

In particular, the solid circles correspond to the percent concentrations of riboflavin when the corneal tissue 101 is subjected to UV-A radiation of 3 mW/cm².

The empty circles, by contrast, correspond to the percent concentrations of riboflavin when the corneal tissue 101 is subjected to UV-A radiation of 10 mW/cm².

The continuous lines are the result of a fit with an exponential law, which mathematically defines the variation in the riboflavin concentration, c(t), during the UV-A irradiation, i.e.:

$$c(t) = c_0 \exp\left(-\frac{t}{t_{rate}}\right) + y_0$$

where $c_0$ is the concentration of riboflavin administered in the corneal tissue 101 at the time t=0 and having a value above $T_{h1}$, i.e. prior to the UV-A irradiation. The inverse of the parameter $t_{rate}$ describes the velocity of riboflavin consumption in the corneal tissue 101 due to exposure to the UV-A radiation and $y_0$ is a fit parameter.

Figure 5:
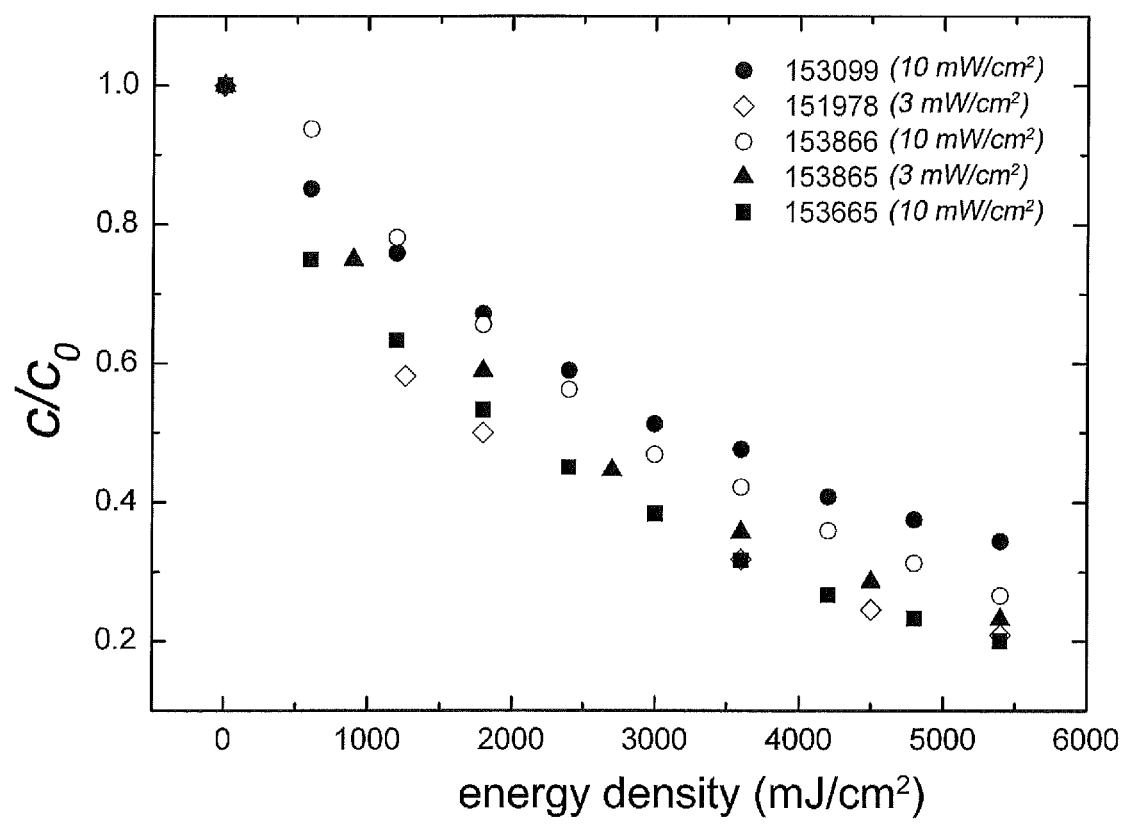
FIG. 5 represents the variations in the riboflavin concentrations normalised to the initial value $c_0$ for a UV-A power density equal to 3 mW/cm$^2$ and 10 mW/cm$^2$ with variations in the radiant energy density (in mJ/cm$^2$)

FIG. 5 shows the variations in the riboflavin concentration normalised to the initial value $c_0$ for both UV-A power densities (3 mW/cm² and 10 mW/cm²) used for different corneal tissues (indicated with different numbers and symbols) with variations in the irradiated energy density (in mJ/cm²).

It is well known that a corneal cross-linking treatment induces the generation of further chemical bonds between the amino acids of corneal tissue proteins (photopolymerization). This process induces a mechanical stiffening of the corneal tissue. In order to be clinically effective, a corneal cross-linking treatment must impart to the corneal tissue a biomechanical stability such as to withstand physiological ocular stresses (e.g. intraocular pressure).

Now, with the present invention, the efficacy of a cross-linking treatment can be estimated based on the value of the riboflavin concentration reached prior to the photo-activation thereof (indicated as C) and the concentration value after photo-activation (indicated as C').

Preferably, the processing unit 4 is further configured to evaluate the clinical efficacy of the cross-linking treatment on the treated corneal tissue 101 on the basis of two input parameters: the riboflavin concentration reached prior to the photo-activation thereof C and the percent consumption of the riboflavin, calculated as: consumption$_\%$=(C−C')/C.

Figure 6:
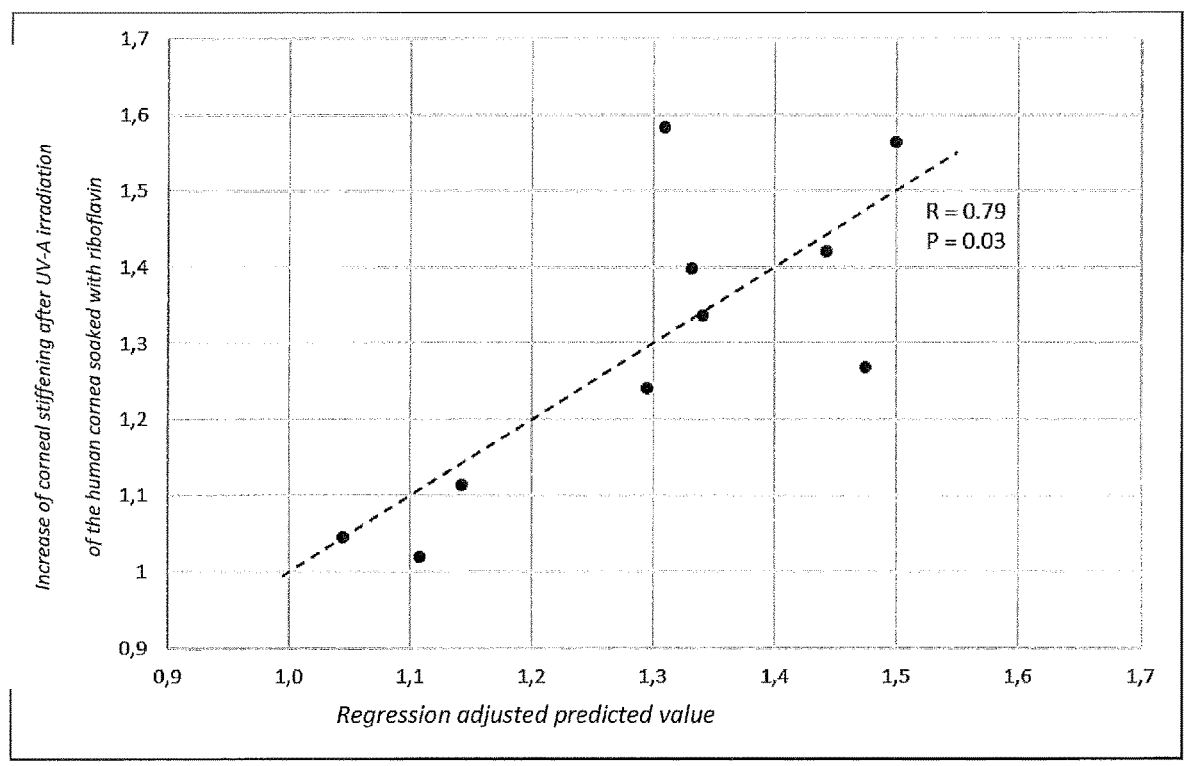
FIG. 6 illustrates a multiple linear regression model which correlates the predicted increase in mechanical stiffness on corneal tissue subjected to the cross-linking treatment with the concentration and percent consumption of the chromophoric agent.
Figure 7:
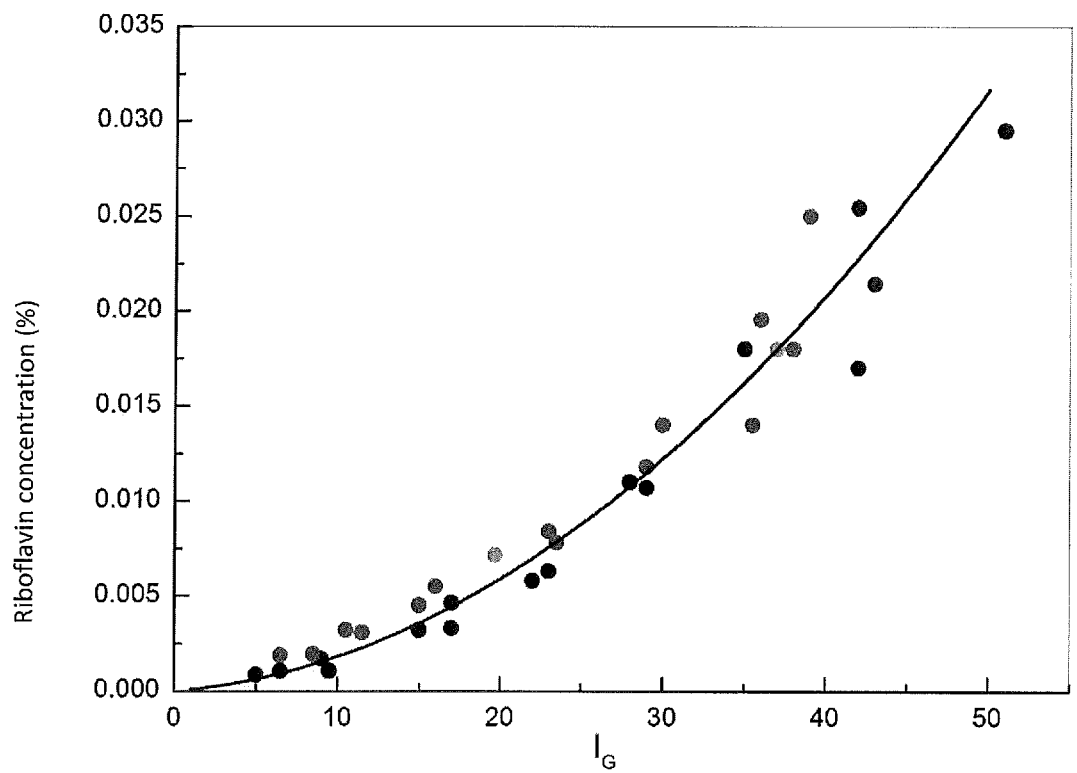
FIG. 7 represents the curve of the percent concentration of riboflavin (y-axis) as a function of the average intensity of the green pixels ($I_G$) of the image of corneal tissue acquired by an RGB video camera, obtained experimentally during a procedure of calibration of the apparatus of FIG. 1.
Figure 8:
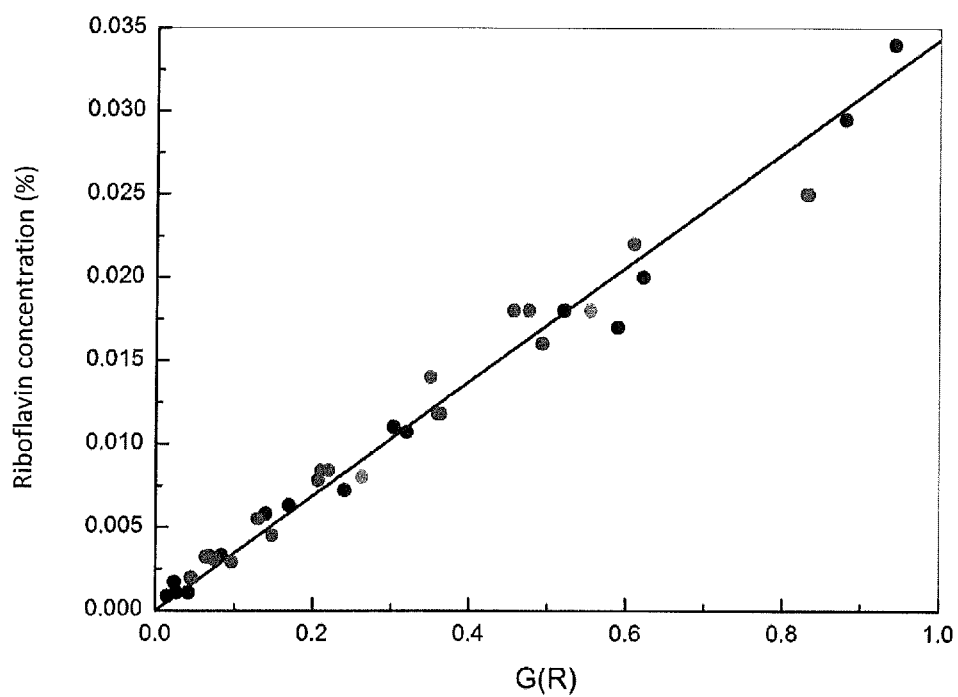
FIG. 8 represents the curve of the percent concentration of riboflavin (y-axis) with variations in the value of the function G(R), which depends on the values of the average intensity of the blue pixels of the image of corneal tissue acquired by an RGB video camera, obtained experimentally during a procedure of calibration of the apparatus of FIG. 1.

FIG. 6 represents, by way of example, the multiple linear regression model which correlates the predicted increase in mechanical stiffness in the corneal tissue 101 subjected to the above-described cross-linking treatment with the two regression variables: the concentration C and the consumption % of the chromophoric agent 100. In the cross-linking treatment, UV-A radiation with a power density of 3 mW/cm² was applied for 30 minutes.

The experimental results (black circles) in FIG. 6 were obtained using the apparatus 1 to carry out the above-described process (including the cross-linking treatment) jointly with a biomechanical test apparatus or an atomic force microscope, which provides the values of the Young modulus for each tissue treated.

Specifically, the increases in mechanical stiffness induced in the corneal tissue 101 by the cross-linking treatment are indicated on the y-axis, whilst the x-axis shows the values of the mechanical stiffening Y of the corneal tissue predicted by the model described according to the equation:

$$Y = \square_0 + \square_1 * C + \square_2 * \text{consumption}_\%$$

The regression coefficient $\square_0$, $\square_1$ and $\square_2$ are the model parameters by means of which the mechanical stiffening Y of the corneal tissue 101 can be predicted as a function of the values C and consumption % measured during the corneal cross-linking treatment.

The dashed regression line is obtained by means of known mathematical techniques. The model makes it possible to estimate, in a statistically significant manner (R=0.79 and P=0.03, where R is the linear correlation coefficient and P indicates the statistical significance) the increase in the mechanical stiffness of the conical tissue 101.

For the purpose of evaluating the efficacy and safety of the cross-linking treatment, the cross-linking treatment cycle comprises:
  switching on the first source 2;
  adjusting the intensity of the first source 2 so that the power density $S_{21}$ is equal to or greater than the first safety interval (so as to activate the chromophoric agent 100);
  subjecting the corneal tissue 101 containing the chromophoric agent 100 to the first electromagnetic radiation 21;
  performing a further measurement of the fluorescence intensity 31 issued by the corneal tissue 101 containing the chromophoric agent 100
  switching off the first source 2;
  switching on the second source 12;
  adjusting the intensity of the second source 12 so that the power density $S_{212}$ is equal to the second safety interval;
  subjecting the corneal tissue 101 containing the chromophoric agent 100 to the second electromagnetic radiation 212;
  performing a further measurement of the intensity diffused 313 by the corneal tissue 101 containing the chromophoric agent 100;
  calculating the factor C of concentration of the chromophoric agent 100 inside the corneal tissue 101 using the measurement and the further measurement of the fluorescence intensity 31 and of the diffused intensity 313;
  estimating the value of the mechanical stiffening Y of the corneal tissue 101 as long as it remains below a threshold of efficacy $Y_h$.

Based on values of the riboflavin concentration prior to photo-activation (C) and after photo-activation (C') and the associated biomechanical values of the conical tissue 101, a two-dimensional map is created to assess the efficacy of the cross-linking treatment, whose values range between 0 (ineffectiveness of the treatment) and 1 (maximum efficacy of the treatment).

Figure 9:
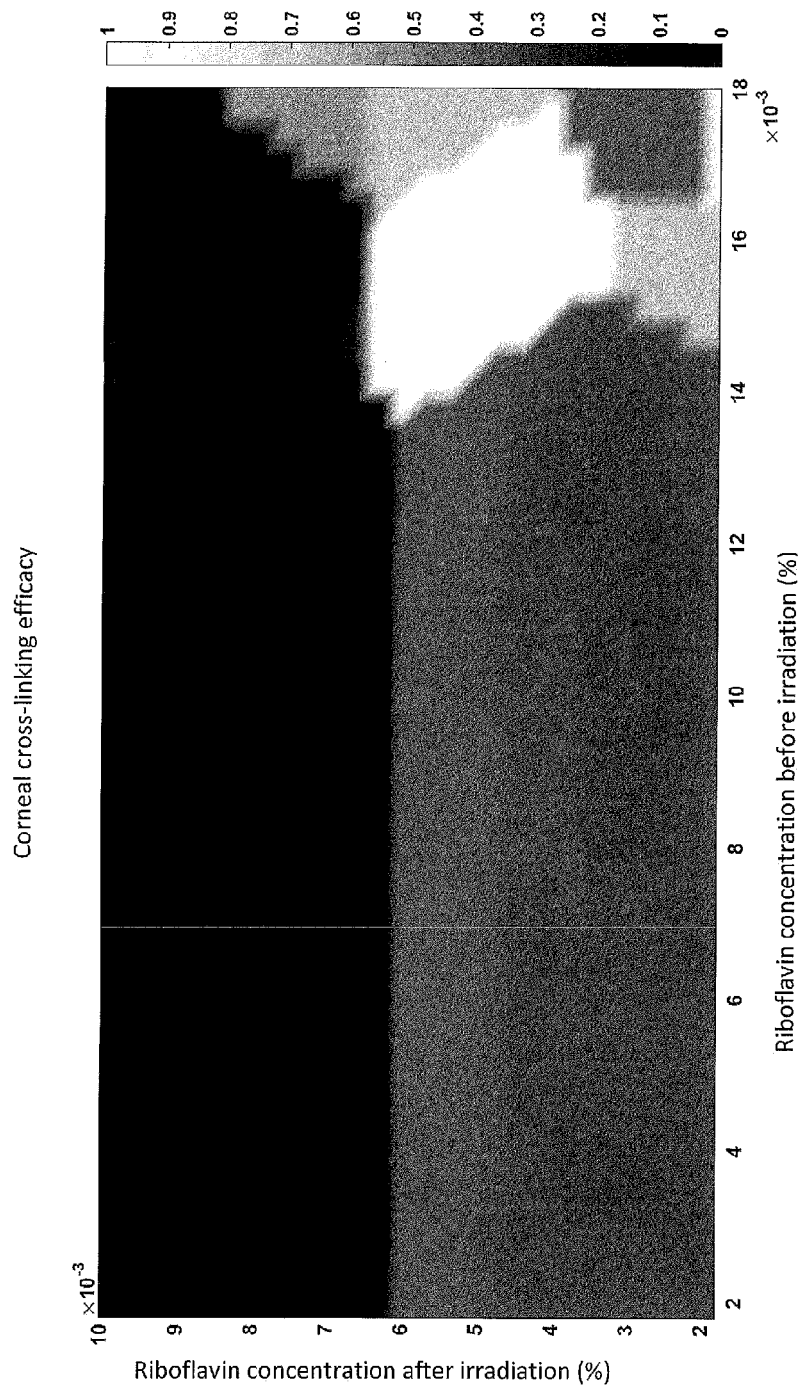
FIG. 9 represents a map of the efficacy of the conical cross-linking treatment according to the present invention.

The map, illustrated in FIG. 9, shows the operator the increase in the clinical efficacy of the cross-linking treatment in real time and teaches when the treatment reaches the maximum efficacy for the cornea undergoing treatment. In particular, the efficacy values on the map are shown with a probability colour scale that ranges linearly from 0 (not effective, black) to 1 (maximum efficacy, white).

The efficacy map is automatically updated by means of a machine learning algorithm, on the basis of the values acquired during use of the control apparatus 1. The map is capable of instructing the operator in real time during the performance of the cross-linking treatment in order to assure the efficacy and safety thereof in a reliable and efficient manner, irrespective of the treatment protocol the operator is following.

In one variant, the process proposed herewith comprises modifying the pattern of photo-activating intensity of the first electromagnetic radiation 21 via the collimating means 5 during the corneal cross-linking treatment (comprising dosing and photo-activation of the chromophoric agent).

This procedure envisages the possibility of iteratively modifying the spatial pattern of photo-activating intensity of the first source 2 as long as the value of clinical efficacy of the corneal cross-linking treatment exceeds the threshold of efficacy of the treatment.

From the description made, the features of a control apparatus for controlling the dosing of a chromophoric agent in a corneal tissue and of a process for dosing a chromophoric agent in a corneal tissue, according to the present invention, appear clear, as do the advantages thereof.

In particular, the dosing of the chromophoric agent in the corneal tissue is controlled in real time by monitoring at least one spectroscopic parameter (fluorescence or diffused intensity) representative of the interaction between the electromagnetic radiation and the corneal tissue.

The concentration of the chromophoric agent can be monitored both before and during the photo-activating step of the cross-linking treatment, a fact which enables the administration of the agent to be interrupted and the photo-activation of the agent be interrupted or continued in order to stiffen the corneal tissue in a personalised manner. This monitoring enables the cross-linking treatment to be personalised on the basis of the specific ocular tissue.

The apparatus and process can also be used by ophthalmologists who are not experts in cross-linking treatments (or, in general, not experts in corneal surgery), as the dosing of the chromophoric agent is constantly monitored, so that the operator is guided to interrupt or continue the administration and interrupt or continue the photo-activation of the cross-linking agent in the corneal tissue.

Furthermore, the proposed apparatus enables the efficacy and safety of the cross-linking treatment to be evaluated in real time immediately after the photo-activation based on the concentration of the chromophoric agent administered on the tissue and the consumption of the concentration of the chromophoric agent.

In practical terms, measuring the concentration of the chromophoric agent (e.g. riboflavin) before photo-activation and during photo-activation enables the clinical efficacy of the corneal cross-linking treatment to be determined dynamically (i.e. during the performance of the treatment).

The invention claimed is:

1. A method of cross-linking of a corneal tissue, comprising the steps of:
  subjecting the corneal tissue to at least a first electromagnetic radiation;
  performing a measurement of a first spectroscopic parameter, which is indicative of the energy perturbation caused by the first electromagnetic radiation in the corneal tissue;
  performing at least the following steps in chronological order and, as long as a factor representative of a concentration of a chromophoric agent in the corneal tissue remains below a first pre-established threshold, cyclically repeating at least the following steps:
    administering the chromophoric agent to said corneal tissue;
    subjecting the corneal tissue containing the chromophoric agent to the first electromagnetic radiation with a power density within a first safety interval for the corneal tissue that is selected in such a way that the first electromagnetic radiation does not photo-activate the chromophoric agent;
    performing a further measurement of the first spectroscopic parameter, which is indicative of the energy perturbation caused by the first electromagnetic radiation in the corneal tissue-containing the chromophoric agent;
    calculating said factor representative of the concentration of the chromophoric agent inside the corneal tissue as a function at least of the measurement and the further measurement of the first spectroscopic parameter,
  after said factor representative of the concentration of the chromophoric agent in the corneal tissue equals or exceeds the first pre-established threshold, irradiating said chromophoric agent by said first electromagnetic radiation with a power density able to photoactivate said chromophoric agent as long as the following exponential concentration function c(t) remains above a second pre-established threshold:

$$c(t) = c_0 \exp\left(-\frac{t}{t_{rate}}\right) + y_0$$

where $c_0$ is the concentration of the chromophoric agent administered in the corneal tissue prior to a beginning of said photo-activating at the time t=0, $t_{rate}$ is a parameter whose inverse describes the velocity of consumption of the chromophoric agent in the corneal tissue due to photo-activation and $y_0$ is a fit parameter.

2. The method according to claim 1, wherein said chromophoric agent is a fluorophore, said first electromagnetic radiation having a wavelength selected so as to cause the fluorescence effect of said chromophoric agent, said first spectroscopic parameter being the fluorescence intensity, so that the measurement of the first spectroscopic parameter corresponds to a value of the fluorescence intensity of the corneal tissue without the chromophoric agent and the further measurement of the first spectroscopic parameter corresponds to a value of the fluorescence intensity of the corneal tissue containing said chromophoric agent.

3. The method according to claim 2, further comprising the steps of:
  subjecting the corneal tissue without the chromophoric agent to a second electromagnetic radiation having a wavelength selected so as to be absorbed by said chromophoric agent;
  performing a measurement of the intensity diffused by the corneal tissue without the chromophoric agent;
  as long as said factor representative of the concentration is below the first pre-established threshold, cyclically performing also the following steps:
    after performing the further measurement of the first spectroscopic parameter, subjecting the corneal tissue containing the chromophoric agent to the second electromagnetic radiation;

performing a further measurement of the intensity diffused by the corneal tissue containing said chromophoric agent, wherein said calculating the factor representative of the concentration of the chromophoric agent inside the corneal tissue is further a function of the measurement and the further measurement of the diffused intensity.

4. The method according to claim 1, wherein said first electromagnetic radiation has a wavelength selected so as to be absorbed by said chromophoric agent, said first spectroscopic parameter being the diffused intensity, so that the measurement of the first spectroscopic parameter corresponds to a value of the intensity diffused by the corneal tissue without the chromophoric agent and the further measurement of the first spectroscopic parameter corresponds to a value of the intensity diffused by the corneal tissue containing said chromophoric agent.

5. The method according to claim 1, further comprising a step of estimating a mechanical stiffening of said corneal tissue as a function of the concentration of the chromophoric agent in the corneal tissue before the photo-activating step and the concentration of the chromophoric agent in the corneal tissue during said photo-activating step.

6. The method according to claim 5, further comprising iteratively modifying a pattern of photo-activating intensity of said first electromagnetic radiation as long as the estimated mechanical stiffening is below an effectiveness threshold.

7. A control apparatus for controlling a dosing of a chromophoric agent in a corneal tissue subjected to cross-linking, comprising:

first irradiating means for irradiating said corneal tissue with at least a first electromagnetic radiation able to photo-activate a chromophoric agent inside said corneal tissue in order to produce cross-linking;

first measurement means for measuring a first spectroscopic parameter;

a processing unit configured to perform a first measurement of said first spectroscopic parameter before administering chromophoric agent to said corneal tissue and to perform at least another measurement of said spectroscopic parameter after administering chromophoric agent to said corneal tissue and configured to calculate a factor representative of the concentration of the chromophoric agent inside the corneal tissue as a function of said first and at least another measurements and configured to start said photo-activating of the chromophoric agent by said first irradiating means when said factor representative of the concentration of the chromophoric agent exceeds a first concentration threshold and to arrest said photo-activating of the chromophoric agent by said first irradiating means when said factor representative of the concentration of the chromophoric agent falls below a second concentration threshold and configured to calculate a concentration of the chromophoric agent inside the corneal tissue according to the following exponential law:

$$c(t) = c_0 \exp\left(-\frac{t}{t_{rate}}\right) + y_0$$

where $c_0$ is the concentration of the chromophoric agent administered in the corneal tissue prior to a beginning of photo-activation of said chromophoric agent at the time t=0, $t_{rate}$ is a parameter whose inverse describes the velocity of consumption of the chromophoric agent in the corneal tissue due to photo-activation and $y_0$ is a fit parameter.

8. The control apparatus according to claim 7, wherein said first irradiating means comprise a source configured to emit the first electromagnetic radiation with a wavelength selected so as to cause a fluorescence effect, said first measurement means being configured to measure a fluorescence intensity.

9. The control apparatus according to claim 8, wherein said first measurement means comprise an RGB video camera or a spectrometer or one or more photodiodes.

10. The control apparatus according to claim 9, comprising an optical fibre for transmitting said first electromagnetic radiation to the corneal tissue.

11. The control apparatus according to claim 8, wherein said processing unit is configured to estimate a mechanical stiffening of said corneal tissue as a function of the concentration of the chromophoric agent in the corneal tissue before said photo-activation and the concentration of the chromophoric agent in the corneal tissue during said photo-activation.

12. The control apparatus according to claim 7, wherein said first irradiating means comprise a source configured to emit the first electromagnetic radiation with a wavelength selected so as to be absorbed by said chromophoric agent, said first measurement means being configured to measure a diffused intensity.

13. The control apparatus according to claim 7, further comprising:

second irradiating means for irradiating said corneal tissue with a second electromagnetic radiation;

second measurement means for measuring a second spectroscopic parameter, wherein said first irradiating means comprise a first source configured to emit the first electromagnetic radiation with a wavelength selected so as to cause a fluorescence effect and said first measurement means are configured to measure a fluorescence intensity, said second irradiating means comprise a second source configured to emit the second electromagnetic radiation with a wavelength selected so as to be absorbed by said chromophoric agent and said second measurement means are configured to measure a diffused intensity.

14. The control apparatus according to claim 13, wherein said second source is disposed in such a way that the second electromagnetic radiation strikes the corneal tissue forming an angle θ comprised between 0° and 90° relative to the optical axis r of the corneal tissue.

15. The control apparatus according to claim 13, wherein said first measurement means comprise an RGB video camera or a spectrometer or one or more photodiodes.

16. The control apparatus according to claim 15, comprising an optical fibre for transmitting said first electromagnetic radiation to the corneal tissue.

17. The control apparatus according to claim 13, wherein said processing unit is configured to estimate a mechanical stiffening of said corneal tissue as a function of the concentration of the chromophoric agent in the corneal tissue before said photo-activation and the concentration of the chromophoric agent in the corneal tissue during said photo-activation.

18. The control apparatus according to claim 7, comprising an optical fibre for transmitting said first electromagnetic radiation to the corneal tissue.

19. The control apparatus according to claim 7, wherein said processing unit is configured to estimate a mechanical stiffening of said corneal tissue as a function of the concentration of the chromophoric agent in the corneal tissue before said photo-activation and the concentration of the chromophoric agent in the corneal tissue during said photo-activation.

20. The control apparatus according to claim 19, wherein said processing unit is configured to iteratively modify a pattern of photo-activating intensity of said first electromagnetic radiation as long as the estimated mechanical stiffening is below an effectiveness threshold.

21. The control apparatus according to claim 7, wherein the first irradiating means is operable to irradiate the chromophoric agent inside said corneal tissue at a first power density at which the first electromagnetic radiation is able to photo-activate the chromophoric agent and at a second power density within a first safety interval for the corneal tissue that is selected in such a way that the first electromagnetic radiation does not photo-activate the chromophoric agent.

* * * * *